(12) United States Patent
Chisholm

(10) Patent No.: US 10,478,406 B2
(45) Date of Patent: Nov. 19, 2019

(54) HIGH-PH SOLID-STATE EPINEPHRINE FORMULATION

(71) Applicant: HARC Therapeutics AG, Steinhausen (CH)

(72) Inventor: Robert Chisholm, Steinhausen (CH)

(73) Assignee: HARC Therapeutics AG, Zug (CH)

( * ) Notice: Subject to any disclaimer, the term of this patent is extended or adjusted under 35 U.S.C. 154(b) by 0 days.

(21) Appl. No.: 16/355,941

(22) Filed: Mar. 18, 2019

(65) Prior Publication Data

US 2019/0209495 A1 Jul. 11, 2019

(51) Int. Cl.
*A61K 31/137* (2006.01)
*A61K 9/20* (2006.01)
*A61K 9/16* (2006.01)
*A61K 9/19* (2006.01)

(52) U.S. Cl.
CPC .......... *A61K 31/137* (2013.01); *A61K 9/1658* (2013.01); *A61K 9/2018* (2013.01); *A61K 9/2063* (2013.01); *A61K 9/2095* (2013.01); *A61K 9/1611* (2013.01); *A61K 9/1623* (2013.01); *A61K 9/19* (2013.01); *A61K 9/2009* (2013.01)

(58) Field of Classification Search
CPC .. A61K 31/137; A61K 9/2095; A61K 9/2018; A61K 9/2063; A61K 9/1658; A61K 9/19; A61K 9/2009; A61K 9/1623; A61K 9/1611
See application file for complete search history.

(56) References Cited

FOREIGN PATENT DOCUMENTS

| WO | WO2010139752 A2 | 10/2010 |
| WO | WO2016149028 A2 | 9/2016 |
| WO | WO2017066787 A1 | 4/2017 |
| WO | WO2017218918 A1 | 12/2017 |
| WO | WO2018130963 A1 | 7/2018 |

OTHER PUBLICATIONS

Lockey, Stephen, 1:500 Epinephrine in Gelatin, 1941, Lancaster General Hospital, pp. 592-598. (Year: 1941).*

* cited by examiner

*Primary Examiner* — Trevor Love
(74) *Attorney, Agent, or Firm* — Pharmaceutical Patent Attorneys, LLC

(57) ABSTRACT

Epinephrine formulated in aqueous solvent at a basic pH of about 8.5 remains in solid state. My data show that epinephrine formulated at a pH of about 8.5 is surprisingly resistant to oxidation. I here teach how to formulate solid-state epinephrine in basic solution, and how to use solid-state epinephrine to make pharmaceutical dosage forms.

1 Claim, 2 Drawing Sheets
(2 of 2 Drawing Sheet(s) Filed in Color)

HIGH-PH SOLID-STATE EPINEPHRINE FORMULATION

CROSS-REFERENCE TO RELATED APPLICATIONS

None.

STATEMENT REGARDING FEDERALLY-SPONSORED RESEARCH OR DEVELOPMENT

None.

THE NAMES OF THE PARTIES TO A JOINT RESEARCH AGREEMENT

HARC Therapeutics AG (Switzerland) and Catalent UK Swindon Zydis Ltd. (United Kingdom).

REFERENCE TO SEQUENCE LISTING

None.

STATEMENT REGARDING PRIOR DISCLOSURES BY THE INVENTOR OR A JOINT INVENTOR

None.

BACKGROUND

Epinephrine, also known as 4-[(1 R)-1-Hydroxy-2-(methylamino)ethyl]-1,2-benzenediol, is the active principle of the adrenal medulla and an endogenous catecholamine which acts directly on both alpha and beta adrenergic receptors. When used in pharmaceutical compositions, epinephrine can act as a non-selective alpha and beta adrenergic agonist and can work rapidly to improve breathing, stimulate the heart, raise dropping blood pressure, reverse hives, and reduce swelling of the face, lips, and throat. Uses for epinephrine include emergency treatment of allergic reactions (Type 1), including anaphylaxis, induction and maintenance of mydriasis during intraocular surgery, treatment of bronchospasm, sensitivity reactions, cardiac arrhythmias, GI and renal hemorrhage, superficial bleeding, premature labor, hypoglycemia, and cardiogenic, hemorrhagic, and traumatic shock. Epinephrine can also be used to increase blood flow in ACLS during CPR, as an adjunct to local anesthesia, and for radiographic uses.

Epinephrine is soluble in water at acidic pH, yet at neutral or basic pH is insoluble in water. Further, epinephrine at mildly-acidic pH is notoriously vulnerable to oxidative degradation to epinephrine sulfonate, an undesirable contaminant. Given these two constraints, the art thus teaches to formulate epinephrine as an acidic solution at a pH as low as 2. Such solutions are then administered by injection, as a nasal spray etc.

LOBRUTTO, Rosario et al., Pre-Filled Syringe, PCT WO/2018/130963, teaches a pre-filled syringe, an auto-injector device comprising such pre-filled syringe, a method of administering a pharmaceutical composition with such auto-injector device, and a manufacturing method for such auto-injector device. The pre-filled syringe comprises a container and a needle. The container is filled with a solution of epinephrine, a buffer, and water. The disclosure teaches, "The buffer is configured to buffer in a pH range between 3 and 4." See Abstract. This acidic pH assures that the epinephrine active is dissolved into solution and remains stable.

SURAKITBANHARN, Yosyong et al., Stabilization Of Epinephrine Formulations, PCT WO/12017/218918, teaches epinephrine formulations in aqueous solution for medicinal products that enhance the physicochemical stabilities of epinephrine and extend the product shelf life. In some instances, the formulations comprise epinephrine or a salt thereof, a complexing agent, and a "non-sulfite" antioxidant. The epinephrine formulations substantially demonstrated the superior physicochemical stabilities to conventional sulfite formulation of commercial medications currently available. In some instances, sulfite-free formulations further provide further benefit (e.g., safety benefits) to sulfite-sensitive patients. The compositions, methods for preparing the formulations, and methods of using the same (e.g., in the treatment of anaphylaxis) are also provided. The disclosure teaches to use hydrochloric acid to adjust pH to 2.2-5.0. See e.g., [0012], [0015], [0029].

BAILLIE, Alan, J. et al., Stabilised Composition Comprising At Least One Adrenergic Compound, PCT WO/2010/139752, teaches a stabilized composition comprising at least one adrenergic compound and at least one antioxidant selected from the group consisting of a bisulfite, a metabisulfite and a sulfite compound. See e.g., page 2 line 25; page 5 line 2.

KANNAN, Vinayagam et al., Epinephrine Formulations, PCT WO/2016/149028, teaches pharmaceutical compositions comprising epinephrine, methods of administration, and methods of making the same. The patent claims a composition comprising epinephrine and/or salts thereof, a tonicity regulating agent, an antioxidant, a transition metal complexing agent, and a buffer system consisting of a strong acid (i.e., HCl) as a "pH lowering agent" and a combination of tartaric acid and NaOH as a "pH raising agent". To assure that the system maintains an acidic pH, the disclosure teaches the pH raising agent should have a pKa value within the range of about 2 to 5, preferably within the range of about 3 to 4.5, more preferably within the range of about 3.5 to 4.5, and most preferably about 4. Similarly, the disclosure teaches to use a pH raising agent with have a buffer range from a pH of about 2 to 5, preferably from a pH of about 3 to 4.5, and most preferably from a pH of about 3.5 to 4.5. See [0031] to [0032]. This acidic pH assures that the epinephrine active is dissolved into solution.

LEBEDYEVA, Iryna, O. et al., Compounds, Compositions, And Methods Of Making And Using The Same, PCT WO/2017/066787, teaches epinephrine solutions "wherein the pH of the compound of Formula (I) or hydrate thereof ranges from about 3.5 to about 5.5." See e.g., claim 62.

The art thus teaches to formulate epinephrine as an acidic solution at a pH as low as 2, which solutions may be administered by injection, or as a nasal spray etc. Such acidic solutions, however, may be irritating. Further, administering a liquid concomitantly requires the use of e.g., a metered-dose inhaler or a metered-dose injector. Such devices add significantly to the expense of the product. Such devices also greatly increase the number of potential failure modes, a risk which Failure Mode, Effects And Criticality Analysis (FMECA) attempts to reduce. Further, in certain usage environments liquid solution formulations may be unsuitable or unstable.

There is currently a need in the art for improved epinephrine-containing pharmaceuticals. It is an object of the present invention to provide an epinephrine-containing pharmaceutical composition that addresses some of the limitations of present formulations.

BRIEF SUMMARY

I began by developing a liquid formulation as conventional in the art. I had made epinephrine solutions at pH 5 and 6. Accelerated stability testing of these samples confirmed that stability is inversely correlated to pH. Accelerated stability testing showed that my pH 5 samples had levels of epinephrine sulfonate under the limits allowed by pharmaceutical regulations. In contrast, my samples at pH 6 had levels of epinephrine sulfonate three times higher, and exceeding allowable limits.

I then extended the pH range tested and had samples made at pH 7 and 8.5. On stability testing, my pH 7 samples produced a significant level of epinephrine sulfonate. In contrast, my pH 8.5 samples surprisingly had little to no epinephrine sulfonate at all. I thus found that, contrary to the teachings of the art, epinephrine formulated at a pH of about 8.5 is stable.

My discovery provides an entirely new way to formulate epinephrine. At such high pH, epinephrine does not dissolve. Rather, it remains in solid state as particles in suspension. I thus had manufactured tablets made from pH 7 and pH 8.5 suspensions. My tablets confirmed that one can in fact prepare epinephrine as a solid dosage form rather than as a liquid.

I thus here describe and claim formulating epinephrine in solid state at a pH of about 8.5, and using that solid state epinephrine to make solid dosage forms.

BRIEF DESCRIPTION OF THE SEVERAL VIEWS OF THE DRAWINGS

The patent or application file contains at least one drawing executed in color. Copies of this patent or patent application publication with drawing(s) will be provided by the Office upon request and payment of the necessary fees.

FIG. 1 provides color photographs at t=0 and t=24 hours of the suspension of sample number /5 and tablets made from that suspension.

FIG. 2 provides color photographs at t=0 and t=24 hours of the suspension of sample /6 and tablets made from that suspension.

DETAILED DESCRIPTION

Figure 1A:
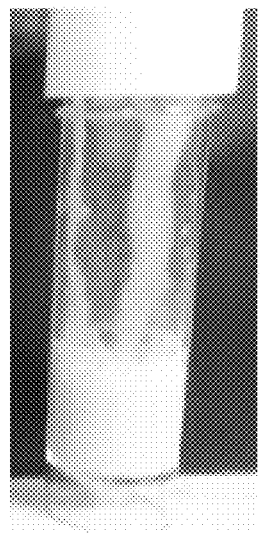
FIG. 1A is the suspension at t=0.

I provide experimental data for my various samples in the following Examples.

Example 1

To test the effect of increased acidity on epinephrine stability, I had prepared epinephrine dissolved in aqueous solvent to make a solution containing 3.33% (w/w) epinephrine in solution, with the pH adjusted to pH 6 for some of my samples and pH 5 for my other samples. I number these samples /1A and /2A respectively. I had my samples assayed when made, and again after one month storage under normal storage conditions and in accelerated condition, and again after two months storage under normal and accelerated conditions. Results for normal storage conditions are show in Table 1.

TABLE 1

| 25° C./60% RH Results Epinephrine in Solution | | | |
|---|---|---|---|
| | Months | | |
| | 0 | 1 | 2 |
| Epinephrine Assay (% label claim) | | | |
| /1A | 95.9 | 96.2 | 96.8 |
| /2A | 100.0 | 98.0 | 99.2 |
| Sodium Metabisulfite (% label claim) | | | |
| /1A | 50.4 | 42.0 | 45.0 |
| /2A | 19.7 | 13.3 | 15.4 |
| Epinephrine sulfonate (% NPA) | | | |
| /1A | 4.46 | 5.91 | 7.75 |
| /2A | 1.51 | 1.32 | 2.00 |
| Limit | 15 | 15 | 15 |
| Total Unknown Impurities (% NPA) | | | |
| /1A | 0.17 | ND | 0.14 |
| /2A | 0.12 | 0.54 | 0.18 |
| Limit | 1 | 1 | 1 |
| Total Impurities (% NPA) | | | |
| /1A | 4.63 | 5.91 | 7.89 |
| /2A | 1.63 | 1.86 | 2.18 |
| Limit | 16 | 16 | 16 |

The data for my samples show that after only one month of storage under normal conditions, my higher-pH sample shows measurably less epinephrine than my lower-pH sample. My higher pH sample continues to show inferior epinephrine content after two months storage. Similarly, my higher-pH sample shows markedly more residual sodium metabisulfite even on initial manufacture (t=0), indicating that it does not effectively complex oxygen free radicals at the higher pH. Similarly, my higher-pH sample shows markedly more epinephrine sulfonate (an undesirable impurity) and more total impurities (including unknown impurities) both on initial manufacture and subsequently. My data confirm the prior art teaching that epinephrine is more stable at lower pH.

Results for sample numbers /1A and /2A for accelerated storage conditions are shown in Table 2.

TABLE 2

| 40° C./75% RH Results Epinephrine in Solution | | | |
|---|---|---|---|
| | Months | | |
| | 0 | 1 | 2 |
| Epinephrine Assay (% label claim) | | | |
| /1A | 95.9 | 86.2 | 86.2 |
| /2A | 100.0 | 94.0 | 93.9 |
| Sodium Metabisulfite (% label claim) | | | |
| /1A | 50.4 | 0.2 | 0.1 |
| /2A | 19.7 | 0.3 | ND |

TABLE 2-continued

40° C./75% RH Results
Epinephrine in Solution

| | Months | | |
|---|---|---|---|
| | 0 | 1 | 2 |
| Epinephrine sulfonate (% NPA) | | | |
| /1A | 4.46 | 19.53 | 19.60 |
| /2A | 1.51 | 6.27 | 7.35 |
| Limit | 15 | 15 | 15 |
| Total Unknown Impurities (% NPA) | | | |
| /1A | 0.17 | 0.40 | 0.79 |
| /2A | 0.12 | 0.68 | 0.58 |
| Limit | 1 | 1 | 1 |
| Total Impurities (% NPA) | | | |
| /1A | 4.63 | 19.94 | 20.39 |
| /2A | 1.63 | 6.95 | 7.93 |
| Limit | 16 | 16 | 16 |

The data for accelerated conditions show that my lower-pH sample retains >90% of its initial ("labeled") amount of epinephrine for at least two months, yet after only one month my higher-pH sample falls below this and thus would be commercially unacceptable. Similarly, my lower-ph sample achieves below the acceptable limits of both epinephrine sulfonate and total impurities, while my higher-pH sample exceeds the acceptable limits for both, and does so quite rapidly, after only one month accelerated storage. These data again confirm the prior art teaching that epinephrine is more stable at lower pH.

Example 1 therefore confirms the prior art teaching that epinephrine is less stable at higher pH, i.e., raising the pH from 5 to 6 renders the solution so unstable as to be entirely unacceptable.

Example 2

In Example 2, no acid/base is added, thus providing a mixture with a pH of about 7. In contrast to Example 1, which employed acidic pH and thus produced true solutions of epinephrine dissolved in solvent, Example 2 uses a neutral pH. The epinephrine thus does not dissolve. Rather, it remains in solid state, suspended (not dissolved) in the solvent system. Sample number /1 used 3.33% (w/w) epinephrine (as used in Example 1). Sample number /2 used 13.33% (w/w) epinephrine. I designate these samples as sample numbers /1 and /2, and provide the formulae for each in Table 3.

TABLE 3

| | Sample Number | | | |
|---|---|---|---|---|
| | /1 | | /2 | |
| Material | % w/w | mg | % w/w | mg |
| Purified water | 87.32% | 130.98 | 78.22% | 117.33 |
| Gelatin (EP/USP/JP) (Fish HMW) | 4.80% | 7.20 | 4.30% | 6.45 |
| Mannitol (EP/USP) | 3.84% | 5.76 | 3.44% | 5.16 |
| Sodium metabisulfite (Ph Eur) | 0.30% | 0.45 | 0.30% | 0.45 |
| Disodium EDTA (Ph Eur) | 0.05% | 0.08 | 0.05% | 0.08 |
| Epinephrine | 3.33% | 5.00 | 13.33% | 20.00 |
| Sucralose micronized NF | 0.35% | 0.53 | 0.35% | 0.53 |
| NaOH | 0.00% | 0.00 | 0.00% | 0.00 |
| Total | 100.00% | 150.00 | 100.00% | 150.00 |

Sample numbers /1 and /2 were not acidic. To confirm that these samples produced solid state epinephrine rather than dissolved epinephrine, I had these samples assayed to determine whether the epinephrine had in fact dissolved into solution and if so, by what amount. I provide these data in Table 4.

TABLE 4

Epinephrine at Neutral pH Remains In Solid State

| | Minimum Stoppage | Suspension Assay Testing | | |
|---|---|---|---|---|
| Sample | (Min30) Epinephrine Content (n = 10) | Theoretical Epinephrine % w/w | Epinephrine % w/w Dissolved | % of Epinephrine Dissolved in Suspension Sample |
| /1 | Mean = 98.1% LC Range: 92.9-101.9% LC % RSD = 3.2% | 3.33 | 0.42 | 12.5 |
| /2 | Mean = 102.0% LC Range: 99.5-104.8% LC % RSD = 1.6% | 13.33 | 0.46 | 3.5 |

These data show that without added acid, only about 0.45% of the total epinephrine dissolves in water at pH 7. The remainder remains in a solid state, suspended in the liquid.

As with my previous samples, I had sample numbers /1 and /2 tested for stability over one month, using both normal and accelerated storage conditions. On normal storage, sample /1 (3.33% w/w epinephrine) showed a markedly higher concentration (as a percentage of the total starting amount of epinephrine) of both epinephrine sulfonate and total impurities. The greater stability of sample number /2 appears due to the fact that it had far more moles of epinephrine at start. It thus was better able to withstand oxidation from the finite moles of oxygen in the formulation.

TABLE 5

25° C./60% RH Results for Solid-State Epinephrine
(Sample Numbers /1 and /2)

| | Months | | |
|---|---|---|---|
| | 0* | 1 | 2 |
| Epinephrine Assay (% label claim) | | | |
| /1 | 101.1 | 100.1 | — |
| /2 | 102.5 | 101.8 | — |
| Sodium Metabisulfite (% label claim) | | | |
| /1 | 68.2 | 58.4 | — |
| /2 | 61.6 | 54.2 | — |
| Epinephrine sulfonate (% NPA) | | | |
| /1 | 2.09 | 4.37 | — |
| /2 | 0.44 | 1.15 | — |
| Limit | 15 | 15 | 15 |
| Total Unknown Impurities (% NPA) | | | |
| /1 | 0.11 | 0.10 | — |
| /2 | NQ | NQ | — |
| Limit | 1 | 1 | 1 |
| Total Impurities (% NPA) | | | |
| /1 | 2.20 | 4.47 | — |
| /2 | 0.44 | 1.15 | — |
| Limit | 16 | 16 | 16 |

*1 month at 5° C. used as a pseudo t = 0 time point

Accelerated stability results reiterate these results. After one month, the 3.33% sample (number /1) displayed so much epinephrine sulfonate and total impurities as to nearly exceed allowable limits.

TABLE 6

40° C./75% RH Results for Solid-State Epinephrine

| | Months | | |
|---|---|---|---|
| | 0* | 1 | 2 |
| Epinephrine Assay (% label claim) | | | |
| /1 | 101.1 | 92.7 | — |
| /2 | 102.5 | 101.0 | — |
| Sodium Metabisulfite (% label claim) | | | |
| /1 | 68.2 | 20.9 | — |
| /2 | 61.6 | 19.5 | — |

TABLE 6-continued

40° C./75% RH Results for Solid-State Epinephrine

| | Months | | |
|---|---|---|---|
| | 0* | 1 | 2 |
| Epinephrine sulfonate (% NPA) | | | |
| /1 | 2.09 | 13.38 | — |
| /2 | 0.44 | 2.99 | — |
| Limit | 15 | 15 | 15 |
| Total Unknown Impurities (% NPA) | | | |
| /1 | 0.11 | 0.23 | — |
| /2 | NQ | NQ | — |
| Limit | 1 | 1 | 1 |
| Total Impurities (% NPA) | | | |
| /1 | 2.20 | 13.61 | — |
| /2 | 0.44 | 2.99 | — |
| Limit | 16 | 16 | 16 |

*1 month at 5° C. used as a pseudo T = 0 time point

Example 2 thus shows that without added acid, only about 0.45% of the total epinephrine dissolves in water at pH 7, and the resulting solid-state epinephrine is vulnerable to oxidation within a short time.

Example 3

In Example 3, I used the same general formula as in Example 2, but specified adding sodium hydroxide to increase the pH of the suspension to 8.5. As with Example 2, I compared 3.33% and 13.33% (w/w) epinephrine. I provide the formulae for Sample numbers /3 and /4 in Table 7.

TABLE 7

| | Sample Number | | | |
|---|---|---|---|---|
| | /3 | | /4 | |
| Material | % w/w | mg | % w/w | mg |
| Purified water | 84.75% | 127.13 | 75.71% | 113.56 |
| Gelatin (EP/USP/JP) (Fish HMW) | 4.80% | 7.20 | 4.30% | 6.45 |
| Mannitol (EP/USP) | 3.84% | 5.76 | 3.44% | 5.16 |
| Sodium metabisulfite (Ph Eur) | 0.30% | 0.45 | 0.30% | 0.45 |
| Disodium EDTA (Ph Eur) | 0.05% | 0.08 | 0.05% | 0.08 |
| Epinephrine | 3.33% | 5.00 | 13.33% | 20.00 |
| Sucralose micronized NF | 0.35% | 0.53 | 0.35% | 0.53 |
| NaOH | 2.57% | 3.85 | 2.51% | 3.77 |
| Total | 100.00% | 150.00 | 100.00% | 150.00 |

Sample numbers /3 and /4 were basic pH. I thus had these samples assayed to determine whether the epinephrine dissolved into solution and if so, by what amount. I provide these data in Table 8.

TABLE 8

Epinephrine at pH 8.5 Remains In Solid State

| | Minimum Stoppage | Suspension Assay Testing | | |
|---|---|---|---|---|
| Sample | (Min30) Epinephrine Content (n = 10) | Theoretical Epinephrine % w/w | Epinephrine % w/w Dissolved | % of Epinephrine Dissolved in Suspension Sample |
| /3 | Mean = 99.9% LC Range: 94.6-104.5% LC % RSD = 3.3% LC | 3.33 | 0.05 | 1.4 |

TABLE 8-continued

Epinephrine at pH 8.5 Remains In Solid State

| | Minimum Stoppage | Suspension Assay Testing | | |
|---|---|---|---|---|
| Sample | (Min30) Epinephrine Content (n = 10) | Theoretical Epinephrine % w/w | Epinephrine % w/w Dissolved | % of Epinephrine Dissolved in Suspension Sample |
| /4 | Mean = 102.3% LC Range: 101.7-105.4% LC % RSD = 1.4% | 13.33 | 0.23 | 1.7 |

These data show that at a basic pH 8.5, only about 0.1% of the total epinephrine dissolves in water—even less than at pH 7. These data show that at pH 8.5, epinephrine remains in a solid state, suspended (not dissolved) in the liquid.

As with my previous samples, I had sample numbers /3 and /4 tested for stability over one month, using both normal and accelerated storage conditions. Surprisingly, both of my samples showed that on normal storage, both samples have a near or complete absence of both epinephrine sulfonate and of total impurities.

TABLE 9

25° C./60% RH Results
Solid State Epinephrine (pH 8.5)

| | Months | | |
|---|---|---|---|
| | 0* | 1 | 2 |
| Epinephrine Assay (% label claim) | | | |
| /3 | 101.2 | 101.5 | — |
| /4 | 103.5 | 102.8 | — |
| Sodium Metabisulfite (% label claim) | | | |
| /3 | 85.3 | 83.3 | — |
| /4 | 84.3 | 82.6 | — |
| Epinephrine sulfonate (% NPA) | | | |
| /3 | NQ | NQ | — |
| /4 | ND | ND | — |
| Limit | 15 | 15 | 15 |
| Total Unknown Impurities (% NPA) | | | |
| /3 | NQ | NQ | — |
| /4 | ND | ND | — |
| Limit | 1 | 1 | 1 |
| Total Impurities (% NPA) | | | |
| /3 | NQ | 0.19 | — |
| /4 | ND | ND | — |
| Limit | 16 | 16 | 16 |

*1 month at 5° C. used as a pseudo T = 0 time point

Even more surprising, my samples continued to achieve such stability even on accelerated storage conditions.

TABLE 10

40° C./75% RH Results
Solid-State Epinephrine At pH 8.5 Is Surprisingly Stable

| | Months | | |
|---|---|---|---|
| | 0* | 1 | 2 |
| Epinephrine Assay (% label claim) | | | |
| /3 | 101.2 | 100.8 | — |
| /4 | 103.5 | 102.8 | — |
| Sodium Metabisulfite (% label claim) | | | |
| /3 | 85.3 | 79.6 | — |
| /4 | 84.3 | 77.9 | — |
| Epinephrine sulfonate (% NPA) | | | |
| /3 | NQ | 0.54 | — |
| /4 | ND | 0.20 | — |
| Limit | 15 | 15 | 15 |
| Total Unknown Impurities (% NPA) | | | |
| /3 | NQ | NQ | — |
| /4 | ND | ND | — |
| Limit | 1 | 1 | 1 |
| Total Impurities (% NPA) | | | |
| /3 | NQ | 0.54 | — |
| /4 | ND | 0.20 | — |
| Limit | 16 | 16 | 16 |

*1 month at 5° C. used as a pseudo T = 0 time point

My samples of Example 3 show a remarkable stability. This stability is surprising in light of prior art teachings that high pH renders epinephrine unstable, and is surprising in light of my own experimental data (Examples 1 and 2) corroborating that. Table 11 provides a direct comparison of Sample numbers /1 to /4 (Examples 2 and 3).

TABLE 11

| | | Sodium Metabisulfite (% LC) | Epinephrine (% LC) | Epinephrine sulfonate (%) | Total Unknown Impurities (%) | Total Impurities (%) |
|---|---|---|---|---|---|---|
| Sample | Time | | | | | |
| /1 | SH0* | 68.2 | 101.1 | 2.09 | 0.11 | 2.20 |
| | SH24 | 51.1 | 98.0 | 1.93 | 0.12 | 2.05 |
| /2 | SH0* | 61.6 | 102.5 | 0.44 | NQ | 0.44 |
| | SH24 | 32.3 | 99.2 | 0.46 | 0.10 | 0.56 |
| /3 | SH0* | 85.3 | 101.2 | NQ | NQ | NQ |
| | SH24 | 82.0 | 98.6 | 0.13 | NQ | 0.13 |
| /4 | SH0* | 84.3 | 103.5 | ND | ND | ND |
| | SH24 | 60.9 | 101.0 | NQ | ND | NQ |

Solid-State Epinephrine at pH 7 and 8.5

*1 month 5° C. stability data used

Example 4

I wanted to determine whether the surprising stability achieved by my samples in Example 3 was due to the high pH or rather due to the sodium metabisulfate or disodium EDTA. In Example 4, I measured the effect of sodium metabisulfate and disodium EDTA on low-concentration (3.33% w/w epinephrine) solid-state suspensions. Example 4 thus used the same general formula as in sample number /1, but omitted sodium metabisulfate and disodium EDTA. Sample number /5 was pH 7. Sample number /6 was pH 8.5. I provide the formulae for Sample numbers /5 and /6 in Table 12.

TABLE 12

| | Sample Number | | | |
|---|---|---|---|---|
| | /5 | | /6 | |
| Material | % w/w | mg | % w/w | mg |
| Purified water | 87.67% | 131.51 | 87.83% | 131.75 |
| Gelatin (EP/USP/JP) (Fish HMW) | 4.80% | 7.20 | 4.80% | 7.20 |
| Mannitol (EP/USP) | 3.84% | 5.76 | 3.44% | 5.16 |
| Sodium metabisulfite (Ph Eur) | 0.00% | | 0.00% | |
| Disodium EDTA (Ph Eur) | 0.00% | | 0.00% | |
| Epinephrine | 3.33% | 5.00 | 3.33% | 5.00 |
| Sucralose micronized NF | 0.35% | 0.53 | 0.35% | 0.53 |
| NaOH | | | 0.24% | 0.36 |
| Total | 100.00% | 150.00 | 100.00% | 150.00 |

As with my previous samples, I had sample numbers /5 and /6 tested for stability over one month, using both normal and accelerated storage conditions. Surprisingly, both of my samples showed that on normal storage, even without added sodium metabisulfate and disodium EDTA, both samples have a near or complete absence of both epinephrine sulfonate and of total impurities.

TABLE 13

25° C./60% RH Results
Solid-State Epinephrine Needs No Anti-Oxidant Nor Chelating Agent

| | Months | | |
|---|---|---|---|
| | 0* | 1 | 2 |
| Epinephrine Assay (% label claim) | | | |
| /5 | 101.2 | 101.5 | — |
| /6 | 102.1 | 101.7 | — |

TABLE 13-continued

25° C./60% RH Results
Solid-State Epinephrine Needs No Anti-Oxidant Nor Chelating Agent

| | Months | | |
|---|---|---|---|
| | 0* | 1 | 2 |
| Epinephrine sulfonate (% NPA) | | | |
| /5 | ND | ND | — |
| /6 | ND | ND | — |
| Limit | 15 | 15 | 15 |
| Total Unknown Impurities (% NPA) | | | |
| /5 | ND | ND | — |
| /6 | ND | ND | — |
| Limit | 1 | 1 | 1 |
| Total Impurities (% NPA) | | | |
| /5 | ND | ND | — |
| /6 | ND | ND | — |
| Limit | 16 | 16 | 16 |

*1 month at 5° C. used as a pseudo T = 0 time point

Even more surprising, my samples continued to achieve such stability even on accelerated storage conditions.

TABLE 14

40° C./75% RH Results
Solid-State Epinephrine Needs No Anti-Oxidant Nor Chelating Agent

| | Months | | |
|---|---|---|---|
| | 0* | 1 | 2 |
| Epinephrine Assay (% label claim) | | | |
| /5 | 101.2 | 102.1 | — |
| /6 | 102.1 | 102.4 | — |
| Epinephrine sulfonate (% NPA) | | | |
| /5 | ND | ND | — |
| /6 | ND | ND | — |
| Limit | 15 | 15 | 15 |
| Total Unknown Impurities (% NPA) | | | |
| /5 | ND | NQ | — |
| /6 | ND | ND | — |
| Limit | 1 | 1 | 1 |

TABLE 14-continued

40° C./75% RH Results
Solid-State Epinephrine Needs No Anti-Oxidant
Nor Chelating Agent

| | Months | | |
|---|---|---|---|
| | 0* | 1 | 2 |
| Total Impurities (% NPA) | | | |
| /5 | ND | NQ | — |
| /6 | ND | ND | — |
| Limit | 16 | 16 | 16 |

*1 month at 5° C. used as a pseudo T = 0 time point

My samples of Example 4 show a remarkable stability, even though these samples have no added anti-oxidant. This stability is surprising in light of prior art teachings that anti-oxidant is necessary even with the low-pH solutions conventional in the art. This stability is particularly surprising in light of the prior art teaching that high pH renders epinephrine unstable, and in light of my own experimental data. (Examples 1 and 2) corroborating that.

Example 5

To determine whether my solid-phase epinephrine suspensions might be able to make solid dosage forms, I had tablets made using the suspension of sample numbers /5 and /6. The solid dosage was made by loading the liquid suspension into an aluminum blister-pack form, freezing under liquid nitrogen and drying to remove water. The resulting lyophilized solid dosage is highly porous, and thus disperses almost instantly in the mouth.

Figure 1B:
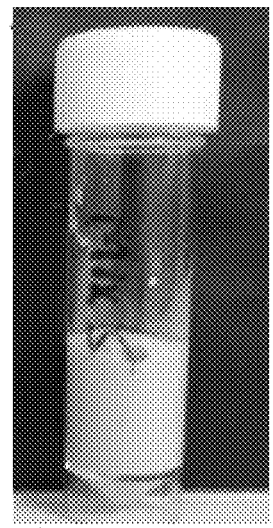
FIG. 1B is the suspension at t=24 hours.
Figure 1C:
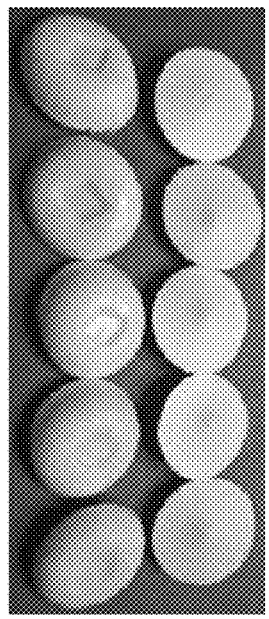
FIG. 1C is tablets at t=0.
Figure 1D:
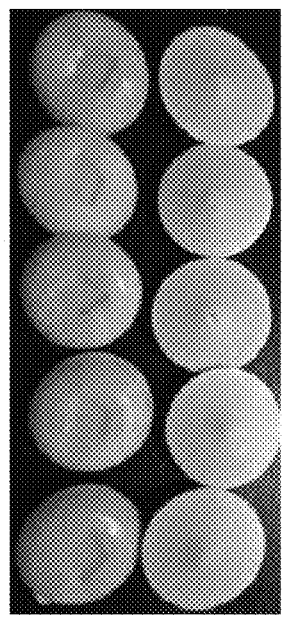
FIG. 1D is tablets at t=24 hours.
Figure 2A:
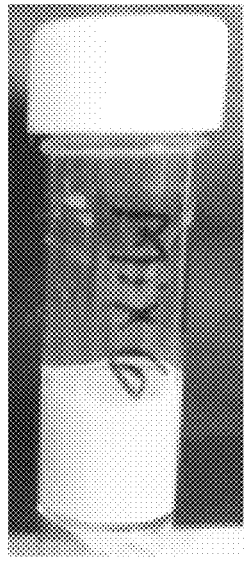
FIG. 2A is the suspension at t=0.
Figure 2B:
FIG. 2B is the suspension at t=24 hours.
Figure 2C:
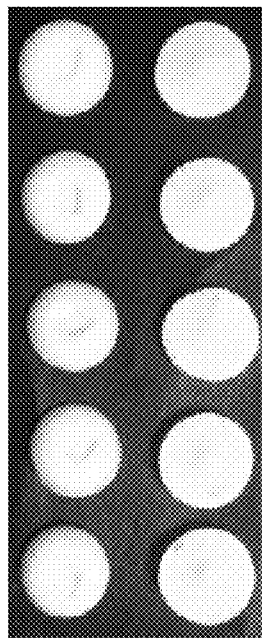
FIG. 2C is tablets at t=0.
Figure 2D:
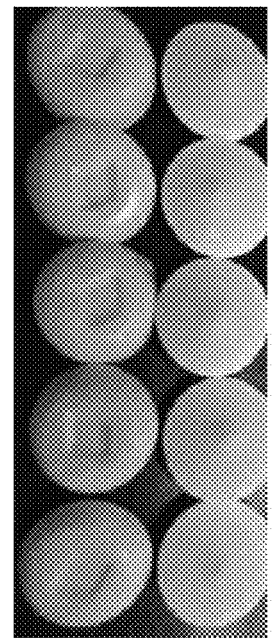
FIG. 2D is tablets at t=24 hours.

FIG. 1 shows color photographs of the suspension of sample number /5, and tablets made from that suspension, at t=0 and t=24 hours. FIG. 2 shows color photographs of the suspension of sample number /6, and tablets made from that suspension, at t=0 and t=24 hours. These photographs confirm that my solid-phase suspensions can be used to make solid dosage forms. These formulae lack anti-oxidant and lack chelating agent. They thus acquire a pink hue (likely due to the formation of adrenochrome). They nonetheless display very little epinephrine sulfonate and very little total impurities.

SUMMARY

Given my disclosure, the artisan can readily make other stable solid formulations of solid-state epinephrine. For example, while many of my samples are at pH 8.5, a higher or a somewhat lower pH would also be suitable, as long as the epinephrine remains in solid state and as long as it retains the surprising resistance to oxidation my samples exemplify. Similarly, while Example 5 uses suspension to make tablets, the artisan can pulverize the resulting freeze dried mass to make an inhalable dry powder equivalent to art-known inhalable liquid epinephrine solutions (e.g., PRIMATENE MIST™ brand epinephrine nasal solution). Similarly, while my Examples produce tablets, one could use solid-state epinephrine in a basic pH solvent system as a liquid dosage form. Similarly, the excipients used in my Examples are not essential for many dosage forms. For example, gelatin is useful to preserve structural integrity of a tablet, but is not needed for a powder. Sucralose is useful as a sweetener for oral dosage forms, but is unnecessary for e.g., inhaled powders. I thus intend the legal coverage of my patent to be defined not by my specific Examples, but by my legal claims and permissible equivalents thereto.

I claim:

1. A process for manufacturing a solid-state epinephrine pharmaceutical dosage form, the process comprising: mixing epinephrine in an aqueous solvent and at least one basic-pH excipient to produce a mixture having a pH of about 8.5, whereby the epinephrine remains in solid state,
   wherein the mixture comprises an antioxidant and a chelating agent,
   wherein the process comprises the step of removing the aqueous solvent to produce a dry dosage form, and
   wherein the dry dosage form is a tablet.

* * * * *